(12) United States Patent
Smith et al.

(10) Patent No.: US 12,350,513 B2
(45) Date of Patent: Jul. 8, 2025

(54) SYSTEMS AND METHODS FOR PHOTOTHERAPY CONTROL

(71) Applicant: RADCLIFFE WATTS, LLC, Mansfield, OH (US)

(72) Inventors: Dan Smith, Mansfield, OH (US); Josh Smith, Annapolis, MD (US)

(73) Assignee: RADCLIFFE WATTS, LLC, Mansfield, OH (US)

( * ) Notice: Subject to any disclaimer, the term of this patent is extended or adjusted under 35 U.S.C. 154(b) by 383 days.

(21) Appl. No.: 17/851,286

(22) Filed: Jun. 28, 2022

(65) Prior Publication Data
US 2022/0409920 A1    Dec. 29, 2022

Related U.S. Application Data

(60) Provisional application No. 63/215,648, filed on Jun. 28, 2021.

(51) Int. Cl.
*A61N 5/06*    (2006.01)
*A61N 5/00*    (2006.01)

(52) U.S. Cl.
CPC ...... *A61N 5/0616* (2013.01); *A61N 2005/002* (2013.01); *A61N 2005/0627* (2013.01); *A61N 2005/0642* (2013.01); *A61N 2005/0644* (2013.01); *A61N 2005/0652* (2013.01); *A61N 2005/0661* (2013.01)

(58) Field of Classification Search
None
See application file for complete search history.

(56) References Cited

U.S. PATENT DOCUMENTS

| | | |
|---|---|---|
| D249,552 S | 9/1978 | Schwartz |
| D284,605 S | 7/1986 | Swanson et al. |
| 5,898,277 A | 4/1999 | Farnsworth et al. |
| 6,087,781 A | 7/2000 | Leppelmeier |
| 6,345,215 B1 | 2/2002 | Drechsler |

(Continued)

FOREIGN PATENT DOCUMENTS

CN    103801007 A    5/2014

OTHER PUBLICATIONS

Written Opinion of the International Searching Authority dated Oct. 25, 2022.
https://daavlin.com/product/hcp/lumera/.

*Primary Examiner* — Shirley X Jian
(74) *Attorney, Agent, or Firm* — Jacob M. Ward; Ward Law Office LLC (57) ABSTRACT

A phototherapy system for treating a user can include an applicator, a controller, and a communication cable configured to couple the applicator and the controller. The applicator can include a light source, a thermal sensor, and a fan. The controller can be in communication with the applicator. The controller can be configured to receive a predetermined treatment regimen to be applied to the user via the applicator. A method for treating skin presenting psoriasis includes providing a phototherapy system. The user can select a skin type on the controller. The use can place the applicator adjacent to the skin presenting psoriasis, eczema, or vitiligo. The user can receive a light therapy treatment from the applicator, whereby the psoriasis, eczema, or vitiligo has been treated.

18 Claims, 10 Drawing Sheets

(56) References Cited

U.S. PATENT DOCUMENTS

| | | | |
|---|---|---|---|
| 7,887,533 B2* | 2/2011 | Barolet | A61N 5/0616 |
| | | | 606/2 |
| 8,206,426 B2 | 6/2012 | Gourgouliatos et al. | |
| 8,435,273 B2* | 5/2013 | Lum | A61N 5/0603 |
| | | | 607/90 |
| 8,486,124 B2 | 7/2013 | Hendrix et al. | |
| 9,764,155 B2 | 9/2017 | Pryor et al. | |
| 9,901,747 B2* | 2/2018 | Gamelin | A61N 5/0616 |
| 9,913,993 B2 | 3/2018 | Gross et al. | |
| 11,311,744 B2* | 4/2022 | Moffat | G16H 20/13 |
| 11,786,748 B2* | 10/2023 | Gamelin | H01L 33/62 |
| | | | 607/94 |
| 11,859,781 B1* | 1/2024 | Liu | F21V 23/0414 |
| 2002/0182563 A1* | 12/2002 | Boutoussov | F21V 7/0008 |
| | | | 433/29 |
| 2005/0154382 A1* | 7/2005 | Altshuler | A61B 18/203 |
| | | | 606/9 |
| 2006/0224217 A1* | 10/2006 | Burgmann | A61N 5/0613 |
| | | | 607/88 |
| 2007/0088410 A1* | 4/2007 | Chung | A61N 5/0621 |
| | | | 607/91 |
| 2007/0276455 A1 | 11/2007 | Fiset | |
| 2008/0027518 A1* | 1/2008 | Island | A61B 18/203 |
| | | | 607/88 |
| 2008/0058783 A1* | 3/2008 | Altshuler | A61N 5/0616 |
| | | | 606/9 |
| 2008/0091250 A1* | 4/2008 | Powell | H05B 45/20 |
| | | | 607/90 |
| 2009/0222068 A1 | 9/2009 | Oberreiter et al. | |
| 2011/0037002 A1* | 2/2011 | Johnson | A61N 5/0613 |
| | | | 250/493.1 |
| 2012/0022618 A1* | 1/2012 | Lum | A61N 5/0603 |
| | | | 607/90 |
| 2012/0059441 A1* | 3/2012 | Chang | A61N 5/0616 |
| | | | 607/90 |
| 2014/0039473 A1* | 2/2014 | Liu | A61B 18/203 |
| | | | 606/9 |
| 2014/0277299 A1* | 9/2014 | Intintoli | A61N 5/0616 |
| | | | 607/94 |
| 2015/0057725 A1 | 2/2015 | Weckwerth et al. | |
| 2016/0136442 A1* | 5/2016 | Zhu | A61N 1/37247 |
| | | | 607/59 |
| 2017/0246475 A1 | 8/2017 | Marchese et al. | |
| 2018/0117355 A1* | 5/2018 | Loupis | A61N 5/0616 |
| 2018/0147415 A1 | 5/2018 | Gross et al. | |
| 2018/0369604 A1 | 12/2018 | Gamelin et al. | |
| 2019/0160303 A1 | 5/2019 | Moffat, IV | |
| 2019/0282826 A1* | 9/2019 | Bellini | A61N 5/0603 |
| 2020/0376292 A1* | 12/2020 | Moffat | G06N 20/00 |
| 2022/0409920 A1* | 12/2022 | Smith | A61N 5/0616 |
| 2024/0156669 A1* | 5/2024 | Spence | A61H 9/0092 |

\* cited by examiner

SYSTEMS AND METHODS FOR PHOTOTHERAPY CONTROL

CROSS-REFERENCE TO RELATED APPLICATIONS

This application claims the benefit of U.S. Provisional Application No. 63/215,648, filed on Jun. 28, 2021. The entire disclosure of the above application is incorporated herein by reference.

FIELD

The present technology relates to phototherapy control and, more particularly, to a phototherapy system and method for treating a user.

INTRODUCTION

This section provides background information related to the present disclosure which is not necessarily prior art.

Use of light to treat medical conditions, otherwise known as phototherapy, dates to the time of ancient Egypt. Phototherapy includes exposure of a subject to either natural sunlight or light generated by an artificial light source in order to treat a lesion, disease, or other condition of the subject. Certain wavelengths or a range of wavelengths of light can be used to provide optimal therapy for particular diseases and conditions.

One type of light source that can be used to generate light in a wavelength suitable for phototherapy includes light emitting diodes (LEDs). An LED comprises a two-lead semiconductor light source, which emits light when activated. When a suitable voltage is applied to the leads of a light emitting diode, energy is released in the form of photons. Modern light emitting diodes may be configured to release photons of various wavelengths, including wavelengths in the ultraviolet range as well as wavelengths in the UVB range.

Phototherapy is currently used to treat a range of disorders and diseases including psoriasis, eczema, and vitiligo. Psoriasis, eczema, and vitiligo are common relapsing remitting skin conditions that affects roughly 14% of the general population. Psoriasis is characterized by red, scaly, itchy skin lesions that may occur anywhere on the body. The causes of psoriasis are not well understood, but it is generally believed to be a genetic disease. Eczema a medical condition in which patches of skin become rough and inflamed, with blisters that cause itching and bleeding, sometimes resulting from a reaction to irritation (eczematous dermatitis) but more typically having no obvious external cause. Vitiligo is a condition in which the pigment is lost from areas of the skin, causing whitish patches, often with no clear cause.

The general pathology of psoriasis, eczema, and vitiligo appears to mediated by an autoimmune response. Immune cells incorrectly identify normal skin cells as pathogenic, and send out cell signals that cause the production of new skin cells. The overgrown skin cells result in lesions typically associated with psoriasis. The exact causes of eczema and vitiligo are unknown but they are generally associated with overactive response of the body's immune cells. No cure currently exists for psoriasis, eczema, and vitiligo and it is difficult to treat in part because of its chronically recurring and remitting nature. However, phototherapy has been successful in the short term.

Unfortunately, there are still many known problems involving the treatment of skin diseases, including psoriasis, eczema, and vitiligo, using various light sources. For example, one issue is that the optical output or radiant flux of an ultraviolet (UV) light-emitting diode (LED) can quickly be diminished as the temperature of the UV LED rises. Research shows that to treat skin disorders, the treatments must have the correct level of energy applied to the skin. In addition, the output power of the LED is inversely proportional to the square of the distance. Undesirably, it is difficult for the user to maintain the distance of a phototherapy applicator. Another known issue is that optical output or radiant flux of a LED is better represented by a gaussian distribution. Each LED type can have its own characteristic, and the radiant flux pattern is typically not uniform. Undesirably, this can result in a non-uniform distribution of optical output to the target skin area. Lastly, the treatments for skin diseases can require precise time intervals and energy levels. Undesirably, the failure to achieve precise time intervals and energy levels can lead to skin burning, skin blistering, and/or low efficacy.

Accordingly, there is a need for a phototherapy treatment system that optimizes the administration of phototherapy, including the provision of precise treatment parameters that minimize the risk of skin burning while at the same time maximize efficacy.

SUMMARY

In concordance with the instant disclosure, ways of providing phototherapy treatments that are precise and that minimize a risk of skin burning, have surprisingly been discovered. The present technology can find particular application to skin presenting psoriasis.

In one embodiment, a phototherapy system for treating a user can include an applicator, a controller, and a communication cable configured to couple the applicator and the controller. The applicator can include a light source, a thermal sensor, and a fan. The controller can be in communication with the applicator. The controller can be configured to receive a predetermined treatment regimen to be applied to the user via the applicator.

In another embodiment, a method for treating skin presenting psoriasis eczema, and vitiligo includes providing a phototherapy system. The phototherapy system can include an applicator and a controller. The applicator can include a light source, a thermal sensor, and a fan. The controller can be in communication with the applicator. The controller can be configured to receive a predetermined treatment regimen to be applied to the user via the applicator. The user can select a skin type on the controller. The use can place the applicator adjacent to the skin presenting psoriasis. The user can receive a light therapy treatment from the applicator, whereby the psoriasis has been treated.

In another embodiment, a system for providing phototherapy to a subject can include a handheld applicator and a portable controller. The handheld applicator can be configured to direct ultraviolet energy to the skin for providing phototherapy. The handheld applicator can include a plastic housing, at least one light-emitting diode (LED), a printed circuit board, a thermal sensor, a heat sink, a variable speed fan, air flow vents, and a power and control connector. It should be appreciated that a skilled artisan can employ different components for the handheld applicator, within the scope of this disclosure.

The plastic housing can be configured to hold and protect the other components. In certain examples, the plastic housing can include two plastic housings. The LED can be configured to produce and direct ultraviolet (UV) light for the phototherapy treatment. In certain examples, the LED can include a plurality of LEDs. As the optical output or radiant flux of an LED can quickly diminish as the temperature of the LED rises, the present technology can thermally control the LED and hence control the UV energy output. In this way, the skin disorder treatment can include a predetermined level of light energy applied to the skin.

In a further embodiment, the portable applicator can be held at a fixed distance from the skin by a plastic housing. Advantageously, the fixed distance provides a defined distribution of light energy to the skin. This can militate the treatment from resulting in an under dosage, skin burning, and/or skin blistering. As the optical output of an LED is better represented by a gaussian distribution, where each LED type can have its own characteristics, the present technology can be used to provide a uniform or substantially uniform radiant flux of light. Multiple LEDs can be arranged in a grid pattern on a printed circuit board. Desirably, this can permit a uniform distribution of radiant flux to a target skin area.

The thermal sensor can detect the temperature of the light source, including where the thermal sensor can be configured to measure the thermal output from one or more LEDs used as the light source. Non-limiting examples of the thermal sensor can include a thermistor, a thermal couple, etc. The portable controller can control the speed of the variable-speed fan to maintain a temperature on the LED. The printed circuit board can have one or more heat sinks, such as thick copper layers. The heat sink can be configured to function as a reservoir for thermal energy. In certain examples, the heat sink can be a high thermally conductive heat sink with fins, where the fins can increase surface area to optimize the exchange of thermal energy with the ambient environment.

The variable-speed fan can be configured to cool the handheld applicator to militate against overheating. In addition, as mentioned previously, the variable-speed fan can maintain a temperature on the LED. The egress airflow vents can be configured to direct airflow to militate against overheating. In certain examples, the handheld applicator can include ingress airflow vents to militate against overheating. The power and control connector can be configured to receive cables for powering the handheld applicator and to receive inputs from the portable controller. It should be appreciated that the present technology can maintain optical radiated flux by its temperature control, heat sinks, and variable fan convection cooling to have a predictable level of power density applied.

The portable controller can be configured to control the handheld applicator. In certain examples, the portable controller can be configured to receive a prescription from the operator. The prescription can initiate sequences of treatment that can militate against wrong time intervals and incorrect energy levels being applied to the targeted skin. Incorrect time intervals and energy levels can lead to skin burning, skin blistering, and/or low efficacy. Advantageously, the prescription can militate against these aforementioned issues.

In yet another embodiment, the portable controller can have a front enclosure, a back enclosure, a printed circuit board assembly, a display, a control input, a DC power input connector, and an applicator power and control connector. The front enclosure and the back enclosure can be configured to protect and store the other interior components. The display can configure to display relevant information to an operator. In certain examples, the display can include a touch screen to permit the operator to interface with the portable controller. For example, the touch screen can permit the operator to input the prescription to the portable controller. The control input can also permit the operator to interface with the portable controller. The DC power input connector can be configured to receive cables for powering the portable controller. The applicator power and control connector can be configured to receive cables to communicate and power with the handheld applicator. In certain examples, the portable controller can further include cables for communication and power purposes and a power supply (AC and/or DC).

Advantageously, the system and method for providing phototherapy to the subject can militate against skin burning, skin blistering, and/or low efficacy. For example, the prescription can initiate sequences of treatment that can militate against wrong time intervals and incorrect energy levels being applied to the targeted skin. In addition, the fixed distance and the grid pattern of the LED can provide phototherapy, while also militating against wrong time intervals and incorrect energy levels being applied to the targeted skin.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present technology relates to a phototherapy system 100 and method 200 for treating psoriasis, shown generally in FIGS. 1-12.

Figure 1:
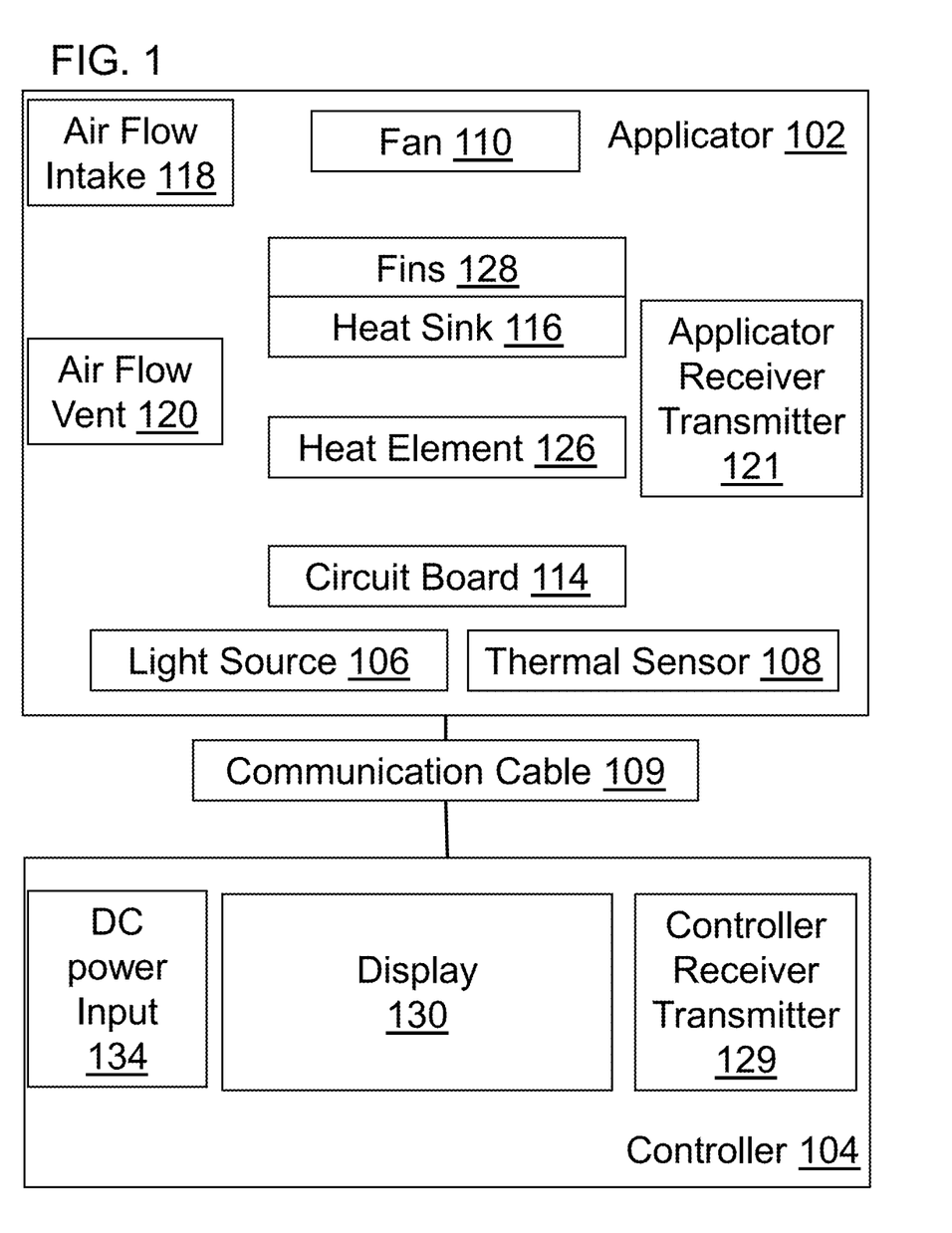
FIG. 1 is a schematic of a phototherapy system.
Figure 2:
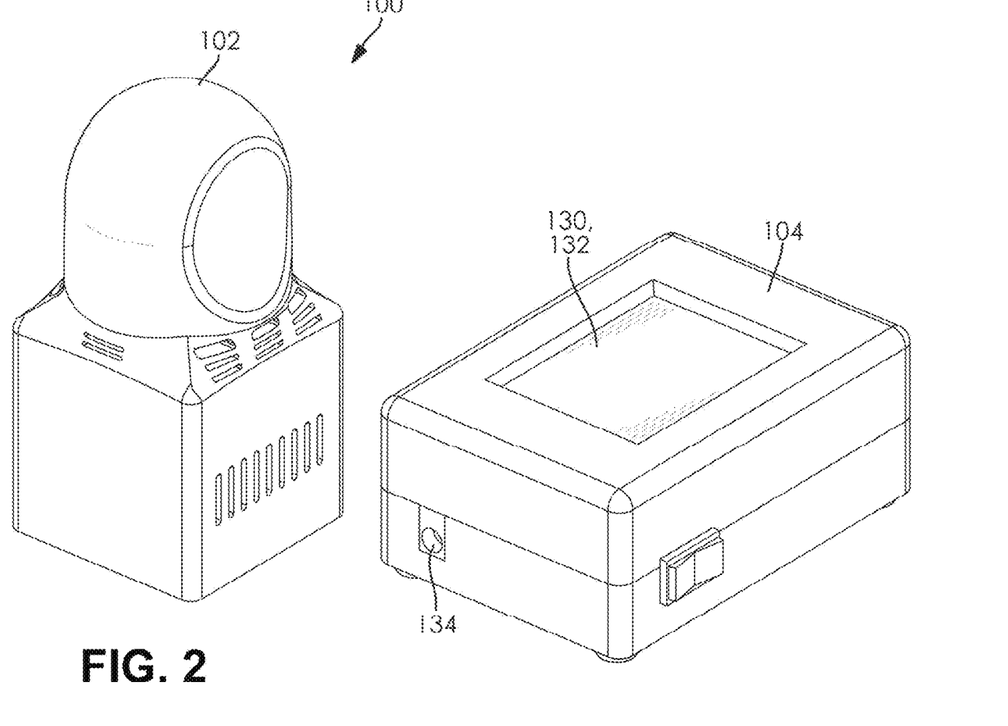
FIG. 2 is a top perspective view of an applicator and a controller.

As shown in FIGS. 1-8, a phototherapy system for treating a user 101 can include an applicator 102 configured to direct ultraviolet energy to the user 101, a controller 104, shown in FIG. 2, and a communication cable configured to couple the applicator 102 and the controller 104. The applicator 102 can include a light source 106, a thermal sensor 108, and a fan 110. The controller 104 can be in communication with the applicator 102. The controller 104 can be configured to receive a predetermined treatment regimen 105, shown in FIG. 12, that can include one or more treatment sessions 107, shown in FIG. 13 to be applied to the user 101 via the applicator 102.

As shown in FIGS. 3-7, the applicator 102 can include a housing 112. The housing 112 can contain the light source 106, the thermal sensor 108, the fan 110, a circuit board 114, a heat sink 116, an air flow intake 118, an air flow vent 120, and an applicator receiver transmitter 121. One of ordinary skill in the art can select suitable components for the phototherapy system 100 to be disposed in the housing 112. The housing 112 can be formed from any rigid material. As a non-limiting example, the housing 112 can be formed from plastic. More specifically, the housing 112 can be formed from polypropylene, high-density polyethylene (HDPE), and polyethylene terephthalate (PETE). One of ordinary skill in the art can select a suitable material for the housing 112.

Figure 5:
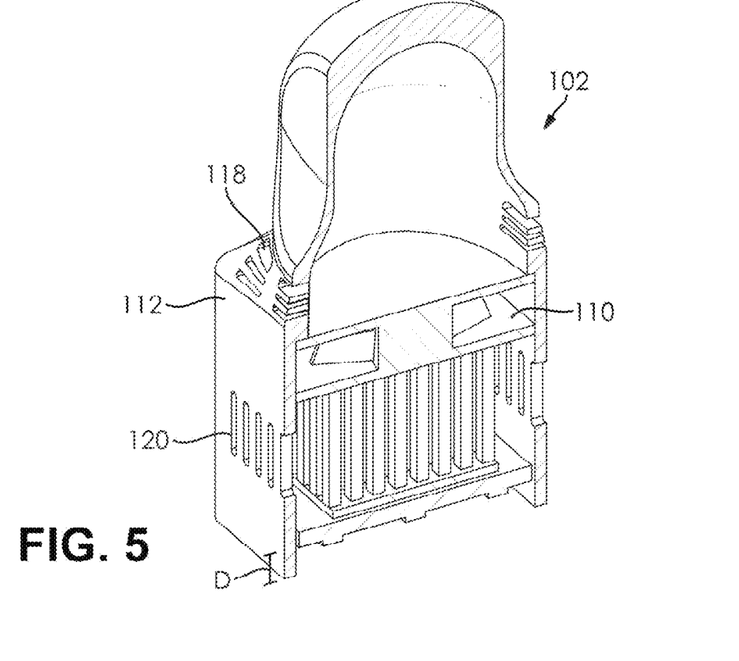
FIG. 5 is a top perspective cross sectional of the applicator taken along line 5-5 in FIG. 4.
Figure 6:
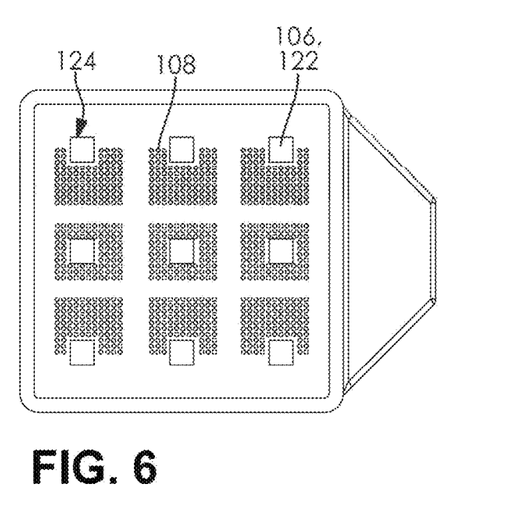
FIG. 6 is a bottom plan view of the applicator.
Figure 7:
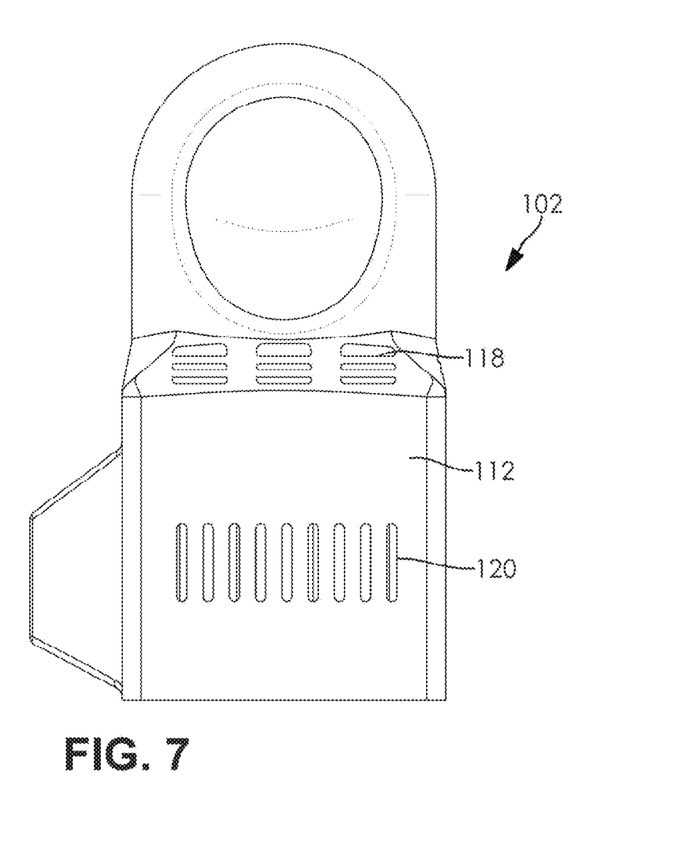
FIG. 7 is a side elevational view of the applicator.

As shown in FIG. 5, the housing 112 can be configured to keep the light source 106 at a predetermined distance (D) within the housing 112 and away from the user 101, in operation. The distance (D) can be dependent upon the pattern of the light source 106 and the intensity of the light source (intensity of UVB). The pattern and spacing of the light source 106 can relate to the predetermined distance that the applicator 102 is placed from the skin. The predetermined distance (D) can militate against the light source 106 being placed too close to the user 101 and burning the user 101 or being placed too far away from the user 101 and resulting in under dosage. As a non-limiting example, the light source 106 can be disposed at distance of about 0.5 centimeters to about 1.5 centimeters within the housing 112. More particularly, the light source 106 can be about 1.0 centimeter within the housing 112. The predetermined distance (D) can be a range larger or smaller than about 0.5 centimeters to about 1.5 centimeters determined by the radiant flux.

One of ordinary skill in the art can select a suitable distance for the light source 106 to be disposed in the housing 112 within the scope of the present disclosure.

Figure 4:
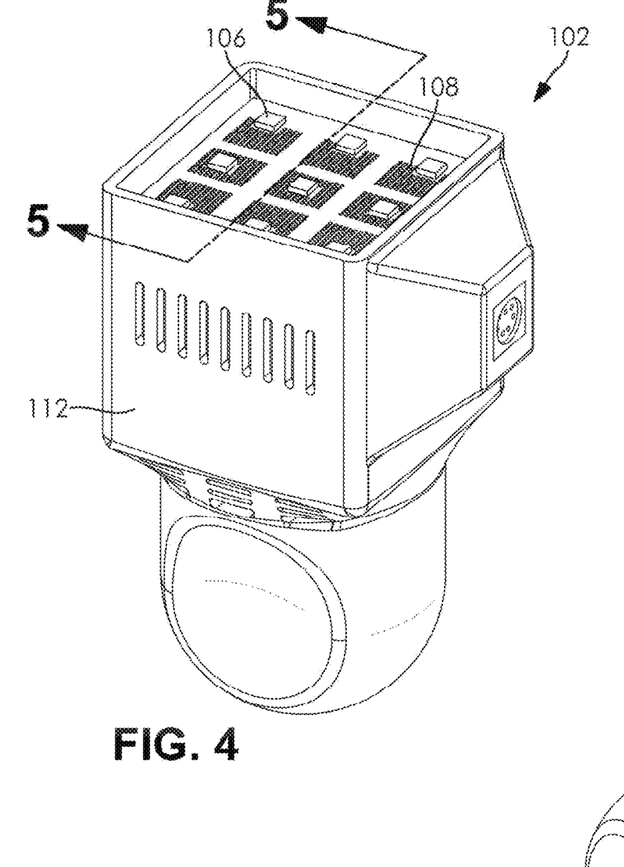
FIG. 4 is a bottom perspective of the applicator.
Figure 10:
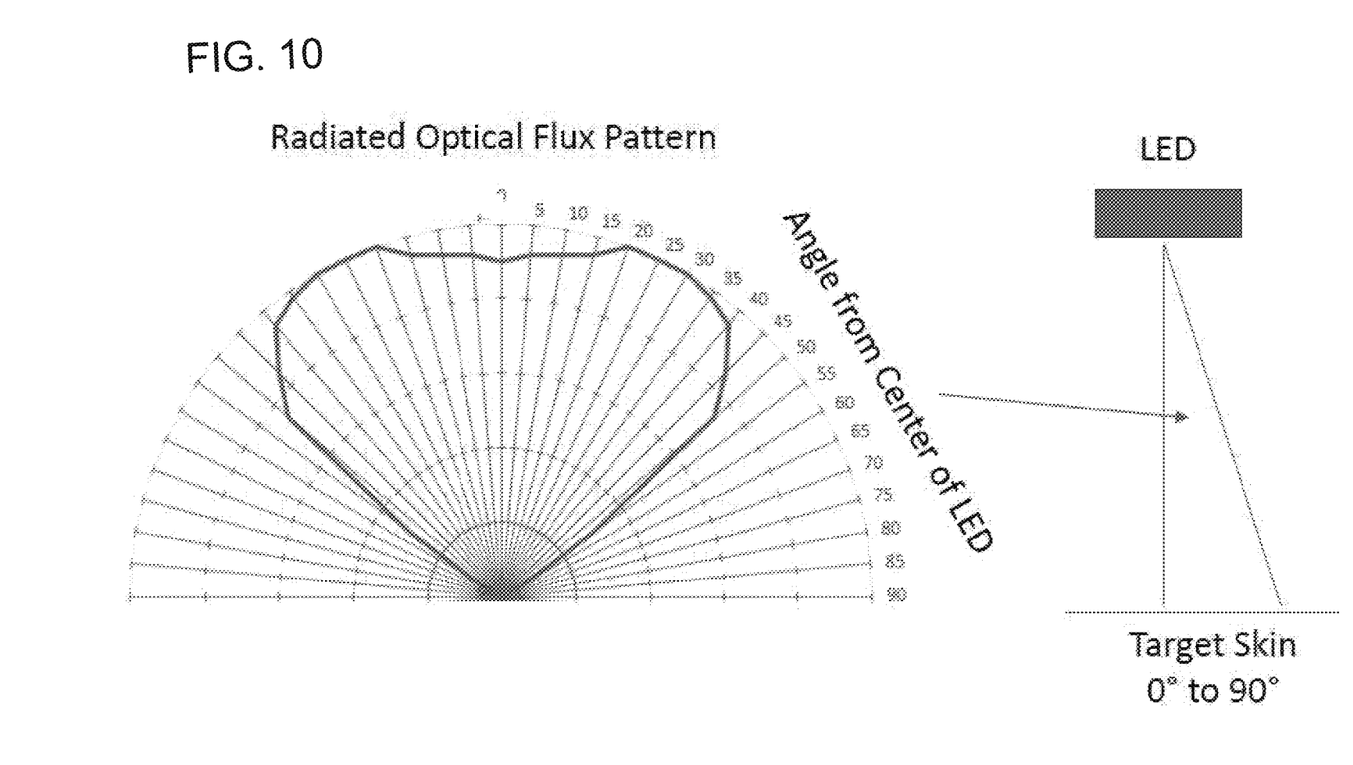
FIG. 10 graphically illustrates a radiated optical flux pattern of a light-emitting diode (LED), as provided by the LED illuminating target skin as shown in a schematic side-elevational view.

With reference to FIG. 4, the light source 106 can include a plurality of light emitting diodes (LEDs) 122. The LEDs 122 can be arranged in a grid pattern 124. It is a known phenomenon that the optical radiated output of certain light sources 106, such as LEDs 122, is represented by a Gaussian distribution. In order to provide consistent treatment from the phototherapy system 100, the energy applied to the skin should be uniform. As shown in FIG. 10, the radiated optical flux pattern from a single LED 122 may not be uniform. Desirably, the grid pattern 124 from multiple LEDs 122 can promote a uniform distribution of optical flux to the user 101 and even light distribution during the treatment session 107. One of ordinary skill in the art can select other suitable patterns for arranging the plurality of LEDs 122 to promote uniform energy distribution across a skin treatment area of a user within the scope of the present disclosure. One of ordinary skill in the art can also select a suitable light source 106 energy within the scope of the present disclosure.

Figure 11:
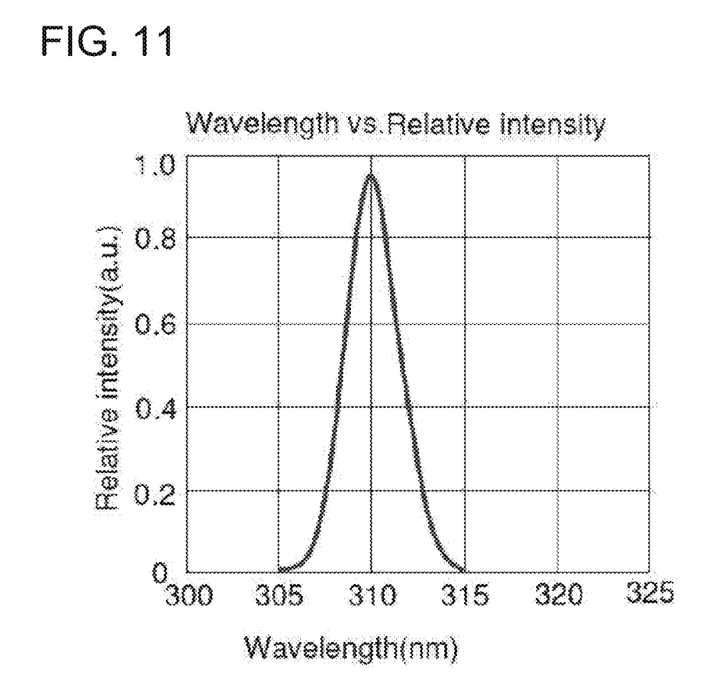
FIG. 11 graphically illustrates a relationship between wavelength and relative intensity.

The plurality of LEDs 122 can emit a wavelength within a predetermined wavelength range. As a non-limiting example, the predetermined wavelength can be in the narrow band UVB range. More specifically, and as shown in FIG. 11, the predetermined wavelength range can include a wavelength between about 305 nanometers and about 315 nanometers. Most specifically, the predetermined wavelength range can include a wavelength of about 308 nanometers or about 310 nanometers. Advantageously, wavelengths within the range of 305 nanometers and 315 nanometers have been shown to be most effective in psoriasis treatment. One of ordinary skill in the art can select other suitable range of wavelength for using phototherapy to treat a user within the scope of the present disclosure. Certain embodiments of the system 100 can include where the wavelengths and wavelength ranges of light emitted by the LEDs 122 can include the values provided herein. Certain embodiments of the system 100 include where the light emitted by the LEDs 122 consists only of the wavelengths and wavelength ranges provided herein. For example, filters (not shown) can be used to select certain wavelengths or wavelength windows of light.

The applicator 102 can include the thermal sensor 108. The thermal sensor 108 can be configured to measure the thermal output from the light source 106. Non-limiting examples of the thermal sensor 108 can include a thermistor and/or a thermal couple. The thermal sensor 108 can be configured to deactivate the light source 106 when the light source 106 exceeds a predetermined temperature. With reference to FIG. 10, it is a known problem that the optical output radiated flux of an ultraviolet LED reduces quickly as the temperature rises. To treat skin disorders, the treatment should preferably have the correct level of energy applied to the skin. The LEDs 122 can produce heat that can increase the temperature and can change the energy output depending on how long the device is used for specific treatment sessions 107. Desirably, the deactivation of the light source 106 at a predetermined temperature can militate against the light source causing a change in the energy output or burning the skin of the user 101. As a non-limiting example, the predetermined temperature can be between about 30° C. and about 40° C. However, the predetermined temperature can be below 30° C. and above 40° C. depending upon the sensitivity of the user and the distance (D) the light source is from the user. One of ordinary skill in the art can select other suitable predetermined temperatures dependent upon the skin sensitivity of the user 101 to militate against a change in energy output or the user 101 receiving a burn.

Figure 8:
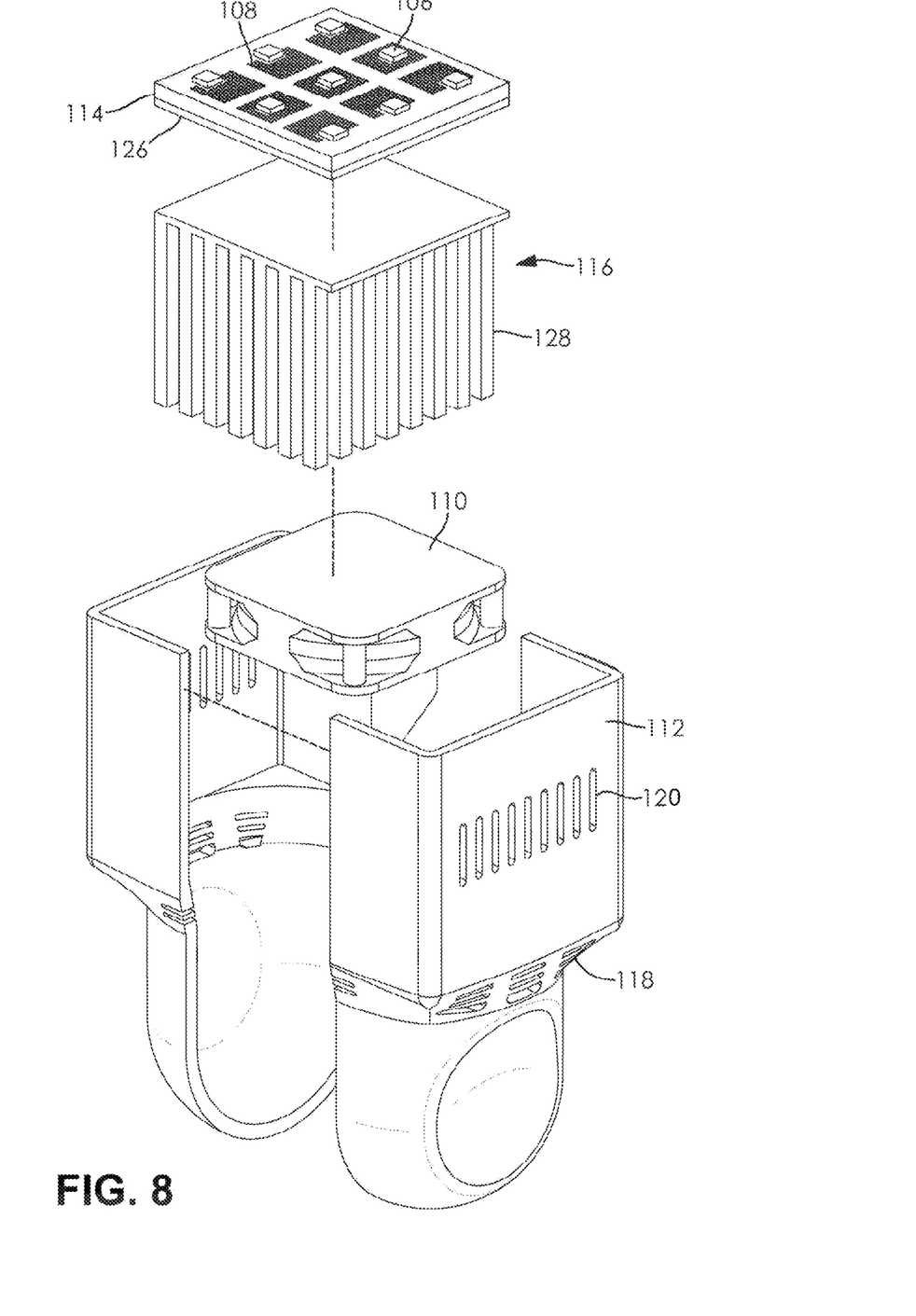
FIG. 8 is an exploded view of the applicator.
Figure 9:
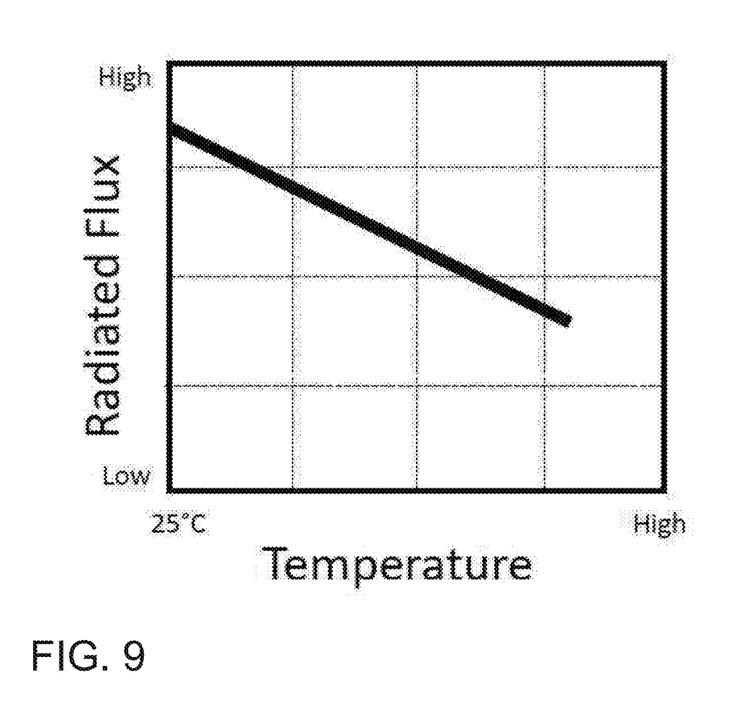
FIG. 9 graphically illustrates a relationship between radiant flux and temperature.

With reference to FIG. 8, the applicator 102 can include the circuit board 114. The circuit board 114 can include a thermal transfer medium 126 configured to interface between the circuit board 114 and the heat sink 116. As a non-limiting example, the thermal transfer medium 126 can be epoxy resin or solder. More specifically, the thermal transfer medium 126 can be a thermal transfer medium with a copper layer (not shown). The copper layer of the thermal transfer medium can militate against thermal strain, therefore militating against the applicator 102 exceeding the predetermined temperature and assisting the applicator 102 in maintaining a constant radiant flux. The circuit board can be disposed adjacent to the heat sink 116. The heat sink 116 can be configured to draw heat away from the circuit board 114 and function as a heat reservoir. As a non-limiting example, the heat sink 116 can be a highly thermal conductive heat sink 116 with fins 128. Further, the heat sink 116 and fins 128 can allow heat created by the light source 106 and the circuit board 114 to divert away from the circuit board 114 and maintain a lower temperature.

The applicator 102 can include the fan 110 configured to act as a cooling system. The fan 110 can be a variable-speed fan configured to militate against overheating. The fan can be configured to maintain the temperature of the applicator 102 and, if the light source 106 temperature exceeds the predetermined temperature, lower the temperature of the light source 106 below the exceeded range. As shown in FIG. 5, the applicator 102 can include the air flow intake 118 and the air flow vent 120. The air flow intake 118 can be configured to allow air to flow into the applicator 102 via the pull of air from the fan 110. As air is pulled into the applicator 102 by the fan 110 through the air flow intake 118, the air is cooled by the fan 110. The air can flow down into the housing 112 of the applicator 102 to cool the heat sink 116 and fins 128. Advantageously, this air flow can aid in maintaining the applicator 102 within the predetermined temperature range and militate against the applicator 102 overheating and either shutting down or burning the user 101.

In another embodiment, the cooling system can be, as non-limiting examples, a Peltier device or a forced convection mechanism. The above-described examples can further militate against the applicator overheating in tandem with the fan 110. One of ordinary skill in the art can select other suitable cooling systems within the scope of the present disclosure.

Figure 3:
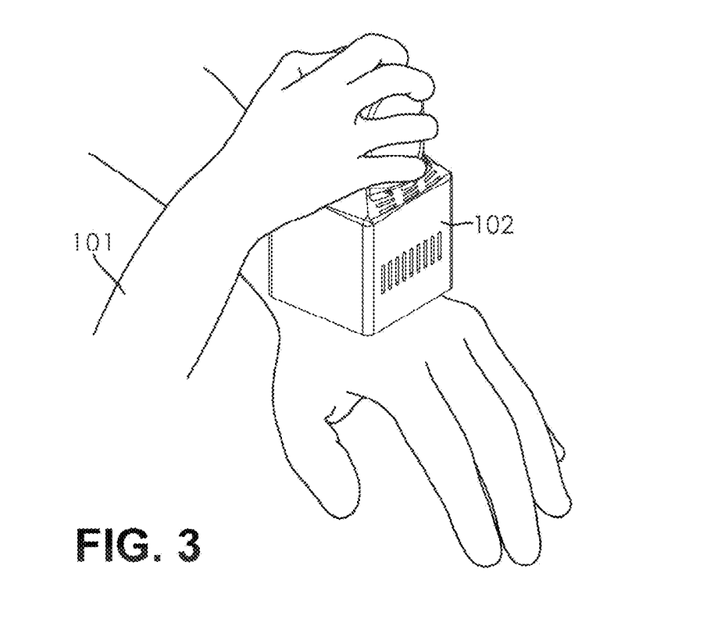
FIG. 3 is a top perspective view of the applicator in use.

As shown in FIG. 3, the controller 104 can be handheld. Advantageously, this can allow the user 101 to administer the predetermined treatment regimen 105 away from a hospital or even their home. The user 101 can administer the predetermined treatment regimen 105 while traveling. Desirably, this can result in consistent and, therefore, more successful treatment.

With reference to FIG. 1, the phototherapy system 100 can include a communication cable 109 configured to couple the applicator 102 and the controller 104. The controller 104 can include a controller receiver transmitter 129. The controller receiver transmitter 129 can be in communication with the applicator receiver transmitter 121 and vice versa via the communication cable 109. In this way, the controller receiver transmitter 129 can send preprogrammed parameters that correspond to the predetermined treatment regimen 105 to the applicator receiver transmitter 121 and can receive operational status updates, such as thermal optics, and the like from the applicator receiver transmitter 121. The controller receiver transmitter 129 and the applicator receiver transmitter 121 can thereby communicate parameters the predetermined treatment regimen 105, including parameters relating to one or more treatment sessions 107. For example, the controller receiver transmitter 129 can send signals to the applicator receiver transmitter 121 for the applicator 102 to execute certain operational steps relative to the predetermine treatment regimen 105 and operation of light source 106 and the controller receiver transmitter 129 can receive signals from the applicator receiver transmitter 121 relative to status and completion of the predetermined treatment regimen 105, as well as status and completion of one or more treatment sessions 107. One of ordinary skill in the art can select other suitable communication means for the applicator receiver transmitter 121 and the controller receiver transmitter 129 within the scope of the present disclosure.

With reference to FIG. 2, the controller can include a display 130. The display 130 can be configured to display relevant information, such as the predetermined treatment regime 105 to the user. The display 130 can include a touch screen 132. The touch screen 132 can permit the user to interface with the controller 104. Further, the controller 104 can be configured to control the fan 110 and to maintain the predetermined temperature of the light source 106. The controller 104 can include a DC power input connector 134. The DC power input connector 134 can be configured to receive cables for powering the controller 104.

The controller 104 can be configured to receive the predetermined treatment regimen 105 to be applied to the user 101 via the applicator 102. The predetermined treatment regimen 105 can initiate treatment sessions 107 relating to a skin type of the user 101. The predetermined treatment regimen 105 that can militate against wrong time intervals and incorrect energy levels being applied to the targeted skin. Incorrect time intervals and energy levels can lead to skin burning, skin blistering, and/or low efficacy. Advantageously, the predetermined treatment regimen 105 can militate against these issues.

Figure 12:
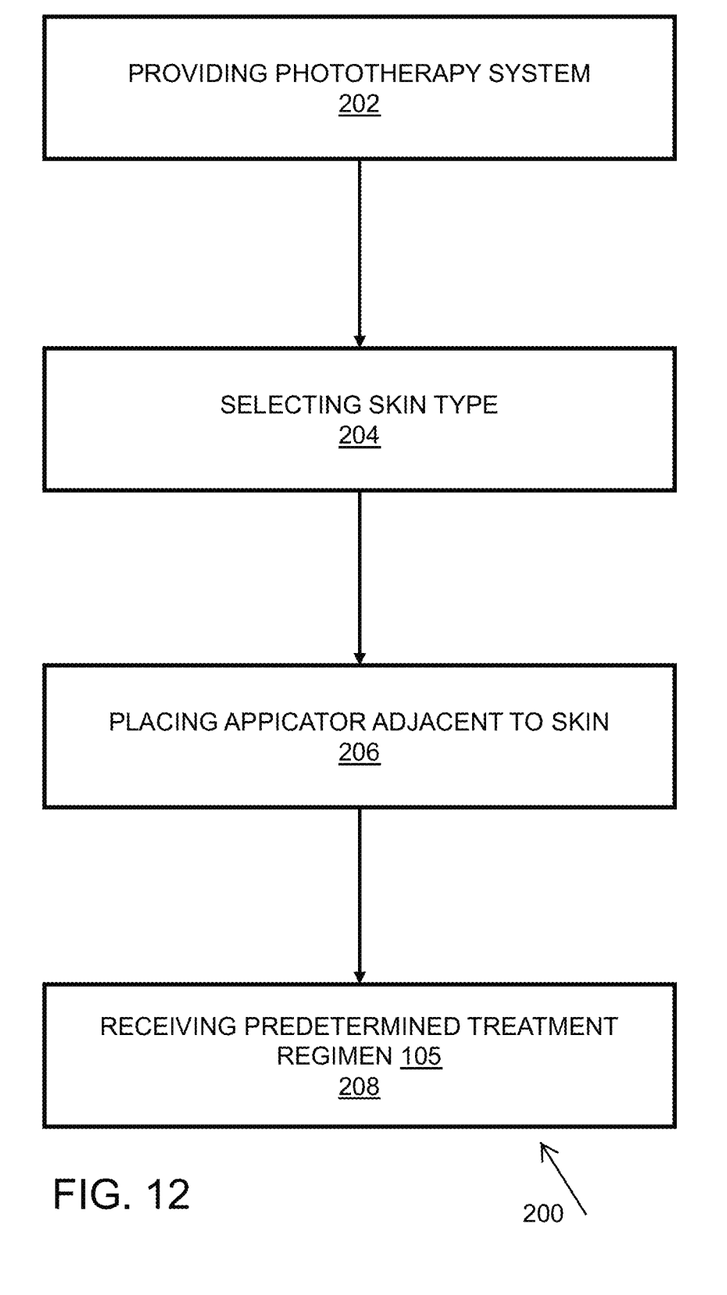
FIG. 12 is a flow diagram illustrating a method for treating skin presenting psoriasis, according to one embodiment.

The present disclosure also contemplates a method 200 for treating skin presenting a skin condition, shown in FIG. 12. The skin condition can be psoriasis, eczema, or vitiligo. One of ordinary skill in the art can select other suitable skin conditions that can be treated using the described method 200. In a step 202, the phototherapy system 100 described hereinafter is provided. A skin type is selected on the controller 104 in a step 204. The user can select one of six skin types, beginning with a first skin type with little pigmentation to a sixth skin type with darker pigmentation, which correspond to one of six predetermined treatment regimens. Each predetermined treatment regimen is individualized to a skin type.

In a step 206, the applicator 102 can be placed adjacent to the skin of the user 101 presenting psoriasis. The user 101 can receive a predetermined treatment regimen 105 from the applicator 102 in a step 208, whereby the psoriasis has been treated. The user can repeat the first four steps of the method every few days over the course of several weeks to complete the predetermined treatment regimen 105 and finish psoriasis treatment in step 210.

Figure 13:
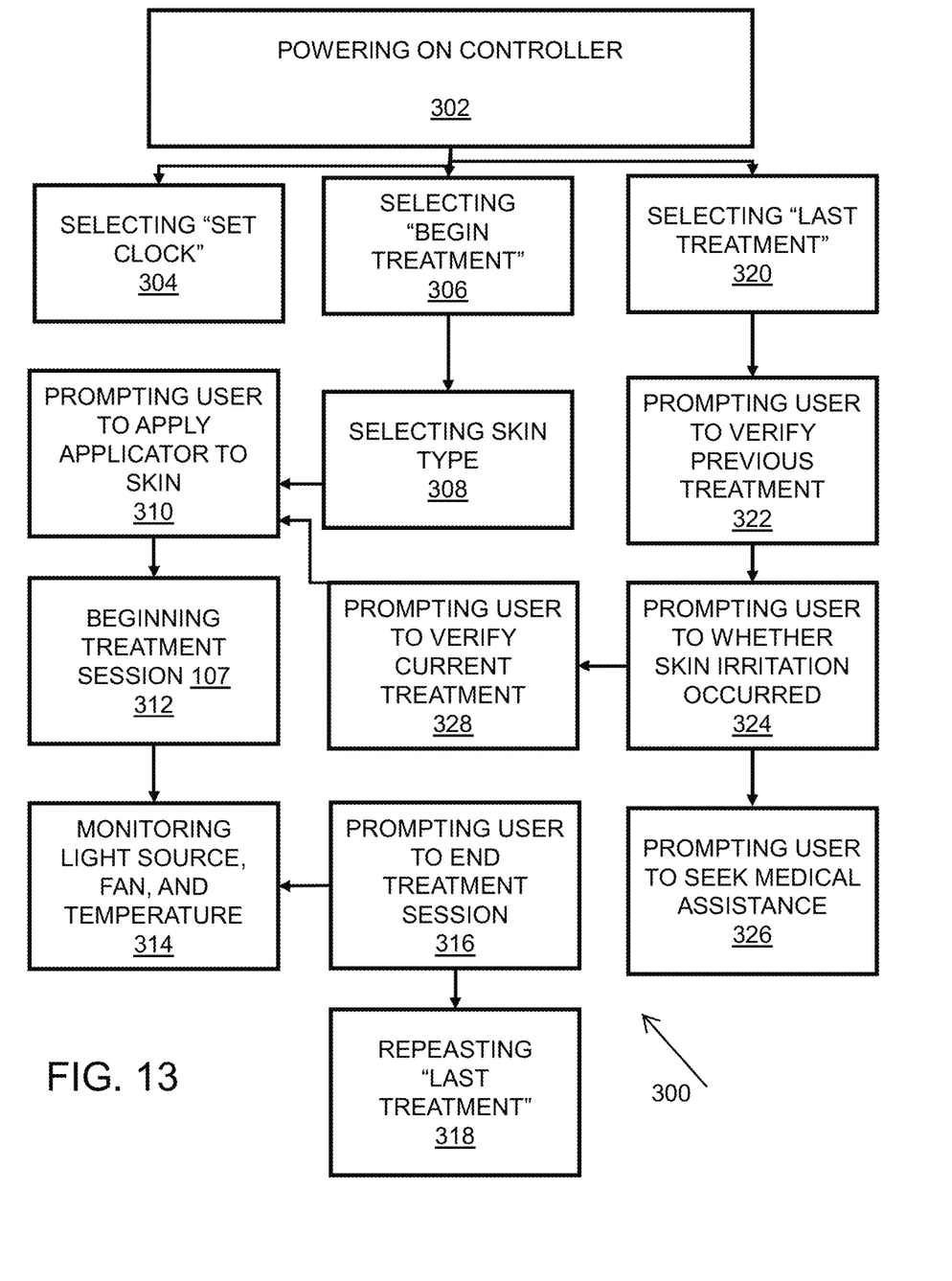
FIG. 13 is a flow diagram illustrating a method of using the phototherapy system in a treatment session, according to one embodiment.

In one embodiment, as shown in FIG. 13, the predetermined treatment regimen 105 can be prescribed by a medical professional and the controller 104 can guide the user 101 through a method 300 of using the phototherapy system in a treatment session 107. In a step 302, the user 101 can power on the controller 104. The user 101 can then select one of three options in a step 302. The first option can include selecting "Set the Clock" to set the date and time in a step 304. Advantageously, setting the date and time can allow the phototherapy system to determine how long it has been between treatment sessions.

The second option can include selecting "Begin Treatment" where a user is beginning the predetermined treatment regimen for the first time in a step 306. In a step 308, the user 101 can select their skin type from a list of six skin types, beginning with a first skin type with little pigmentation to a sixth skin type with darker pigmentation, which correspond to one of six predetermined treatment regimens 105. The controller 104 can prompt the user 101 to apply the applicator 102 to the skin in a step 310. In a step 312, the user can begin a treatment session 107. In a step 314, the phototherapy system 100 can monitor the light source 106, the fan 110, and the temperature of the applicator 102. Where the controller 104 becomes disconnected from the applicator 102, the controller 104 can deactivate the light source 106. Where the temperature of the applicator 102 exceeds the predetermined temperature, the controller 104 can deactivate the light source 106. Where the light source 106, the fan 110, and the temperature of the applicator 102 remain the predetermined temperature range, the applicator 102 can complete the treatment session 107. In a step 316, the controller 104 can prompt the user 101 to treat another area of skin or end the treatment session 107. The user can repeat the "Last Treatment" option over the course of the predetermined treatment regimen in a step 318.

The third option can include selecting "Last Treatment" where a user has previously begun treatment and is resuming the predetermined treatment regimen 105 in a step 320. The controller 104 can prompt the user 101 to verify the previous treatment session 107 in a step 322. In a step 324, the controller 104 can prompt the user 101 as to whether the user 101 experienced skin irritation in a previous treatment session 107. In a step 326, where irritation is present, the controller 104 can prompt the user 101 to seek medical assistance. In a step 328, where irritation is not present, controller 104 can prompt the user 101 to verify the current treatment session 107. The controller 104 can prompt the user 101 to apply the applicator 102 to the skin in a step 310. In a step 312, the user can begin a treatment session 107. In a step 314, the phototherapy system 100 can monitor the light source 106, the fan 110, and the temperature of the applicator 102. Where the controller 104 becomes disconnected from the applicator 102, the controller 104 can deactivate the light source 106. Where the temperature of the applicator 102 exceeds the predetermined temperature, the controller 104 can deactivate the light source 106. Where the light source 106, the fan 110, and the temperature of the applicator 102 remain within the predetermined temperature range, the applicator 102 can complete the treatment session 107. In a step 316, the controller 104 can prompt the user 101 to treat another area of skin or end the treatment session 107. The user can repeat the "Last Treatment" option over the course of the predetermined treatment regimen in a step 318. As a non-limiting example, and as shown in TABLE 1, the user can repeat the "Last Treatment" over the course of up to thirty (30) treatments. One of ordinary skill in the art can select other suitable predetermined treatment regimen durations within the scope of the present disclosure.

In another embodiment, the phototherapy system 100 can keep track of the last treatment session 107 the user 101 completed. Further, the phototherapy system 100 can determine the length of time between treatment sessions 107. The phototherapy system 100 can use the length of time since the last treatment session 107 to determine whether the user 101 should repeat a previous treatment session 107. Where a user 101 has taken an extended amount of time between treatment sessions, the user 101 can lose the progress they have made and be more susceptible to skin burning. Advantageously, the phototherapy system can resume the predetermined treatment regimen 105 at a lower energy treatment session 107 to militate against the user 101 being burned.

Advantageously, the phototherapy system 100 described herein can militate against burning the user 101 and under dosage. This present disclosure provides ways to keep the user 101 safe and promote successful treatment by using a thermal sensor 108 to monitor the temperature of the light source 106 and using the fan 110 and cooling system to maintain a safe temperature. These aspects can improve treatment outcomes and thereby improve psoriasis treatment generally.

In certain embodiments, certain aspects can be included. It is a known problem that the optical output radiated flux of ultraviolet LED reduces quickly as the temperature rises. To treat skin disorders, the treatments must have the correct level of energy applied to the skin. The LEDs 122 produce heat that can drive up the temperature and can change depending on how long the device is used for specific treatment times. The thermal sensor 108 can detect the temperature. The controller 104 can control the speed of the fan 110 to maintain a temperature of the LEDs 122.

The output power of the LED 122 is inversely proportional to the square of the distance (D) between the user 101 and the applicator 102. It can be difficult for the user 101 to maintain the distance (D) of the applicator 102 relative to the skin. The applicator 102 is held at a fixed distance by the housing 112. The fixed distance (D) can maintain a known distance and can provide more accurate application of energy to the skin. This can militate against the potential under dosage, burning of the skin, or blistering.

It is known phenomena that the optical radiated output of the LED 122 is represented by a gaussian distribution. Each LED 122 type can have its own characteristics. In order to have effective treatment session 107, the energy applied to the skin must be uniform. As shown in FIG. 10, the radiated optical flux pattern is not uniform. The pattern of the LEDs 122 can be a grid pattern 124 on the circuit board 114. This can allow for the uniform distribution of optical flux to the skin.

All past devices have used an approach where the user input either time or energy. The approach for this phototherapy system 100 is to input a prescription, defined here as the predetermined treatment regimen 105. The prescription can initiate the sequence of treatment sessions 107 and militate against the potential of wrong time or energy levels to be input into the phototherapy system 100. Incorrect times or energy levels can lead to skin burning, skin blistering, or low efficacy. This approach militates against these problems.

Examples

Example embodiments of the present technology and, more specifically, the predetermined treatment regimen 105 are provided hereinbelow.

The predetermined treatment regimen 105 can be determined based upon six skin types, varying from lightly pigmented skin to heavily pigmented skin, each corresponding to a different predetermined treatment regimen 105. The user can select one of the six skin types. The user can receive several treatment sessions 107 starting at an initial energy corresponding to the skin type selected, with the energy of each treatment session 107 increasing at a constant rate. The light source power can be constant. The duration of each treatment session can be calculated by dividing the energy of the treatment ($mg/cm^2$) by the light source power ($mW/cm^2$). The amount of energy the user receives can increase until the energy reaches a maximum energy corresponding to the specific treatment regimen 105. The maximum energy applied can vary from skin type to skin type. Exceeding the maximum energy can result in over dosage and skin burning. Upon reaching the maximum energy, the user may continue to receive treatment sessions 107 as maintenance treatment or need based on the discretion of a medical practitioner.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A phototherapy system for treating a user, comprising:
   a handheld applicator having an applicator housing including a first end and a second end, the first end including a hemispherical handle for holding the applicator by the user, the applicator including
      a light source disposed at the second end and including a plurality of LEDs arranged in a grid pattern, the plurality of LEDs emitting a wavelength in a narrow band UVB range,
      a thermal sensor, and
      a fan disposed adjacent the hemispherical handle;
   a handheld controller having a controller housing separate from the applicator housing, the handheld controller in communication with the applicator and configured to receive a predetermined treatment regimen to be applied to the user via the applicator, the thermal sensor configured to relay to the controller to deactivate the light source when the light source exceeds a predetermined temperature, the controller further configured to control a speed of the fan to maintain a temperature of the light source; and a communication cable configured to couple the applicator and the controller.

2. The phototherapy system for treating the user of claim 1, wherein the applicator includes an air flow vent configured to divert heat away from the light source.

3. The phototherapy system for treating the user of claim 1, wherein the plurality of LEDs is arranged in a grid pattern.

4. The phototherapy system for treating the user of claim 1, wherein the plurality of LEDs emits a wavelength between 305 nm and 315 nm.

5. The phototherapy system for treating the user of claim 1, wherein the plurality of LEDs emits a wavelength of 308 nm.

6. The phototherapy system for treating the user of claim 1, wherein the plurality of LEDs emits a wavelength of 310 nm.

7. The phototherapy system for treating the user of claim 1, wherein the applicator includes a plastic housing configured to keep the applicator at a predetermined distance from the user.

8. The phototherapy system for treating the user of claim 1, wherein the applicator includes a circuit board.

9. The phototherapy system for treating the user of claim 8, wherein the circuit board includes a thermal transfer medium, the thermal transfer medium configured to cool the circuit board.

10. The phototherapy system for treating the user of claim 9, wherein the applicator includes a heat sink configured to draw heat from the circuit board.

11. The phototherapy system for treating the user of claim 10, wherein the heat sink includes fins.

12. The phototherapy system for treating the user of claim 1, wherein the controller includes a display.

13. The phototherapy system for treating the user of claim 1, wherein the controller is configured to receive a predetermined treatment regimen from the user.

14. The phototherapy system of claim 1, wherein the controller is configured to:

receive a prescription defining the predetermined treatment regimen based on a selected skin type of the user;

initiate a treatment session according to the prescription; and monitor a temperature of the LED during the treatment session using the thermal sensor; and adjust the speed of the fan during the treatment session to maintain the LED at a predetermined temperature range.

15. The phototherapy system of claim 14, wherein the controller is further configured to:

track a time interval between successive treatment sessions;

determine whether-to modify the predetermined treatment regimen based on the time interval; and resume the predetermined treatment regimen at a lower energy treatment session when the time interval exceeds a predetermined threshold.

16. The phototherapy system of claim 1, wherein the hemispherical handle includes a first concave portion and a second concave portion disposed opposite the first concave portion on the hemispherical handle.

17. The phototherapy system of claim 1, wherein the controller includes a display having a touch screen.

18. A method for treating skin presenting a skin condition, the method comprising:

providing a phototherapy system including:

a handheld applicator having an applicator housing including a first end and a second end, the first end including a hemispherical handle for holding the applicator by the user, the applicator including a light source disposed at the second end and including a plurality of LEDs arranged in a grid pattern, the plurality of LEDs emitting a wavelength in a narrow band UVB range, a thermal sensor, and a fan disposed adjacent the hemispherical handle, a handheld controller having a controller housing separate from the applicator housing, the handheld controller in communication with the applicator and configured to receive a predetermined treatment regimen to be applied to the skin presenting psoriasis via the applicator, the thermal sensor configured to relay to the controller to deactivate the light source when the light source exceeds a predetermined temperature, the controller further configured to control a speed of the fan to maintain a temperature of the light source, and a communication cable configured to couple the applicator and the controller;

selecting a skin type on the controller;

placing the applicator adjacent to the skin presenting the skin condition;

applying the predetermined treatment regimen to the skin using the applicator, thereby treating the skin presenting the skin condition.

* * * * *